Figure 1:
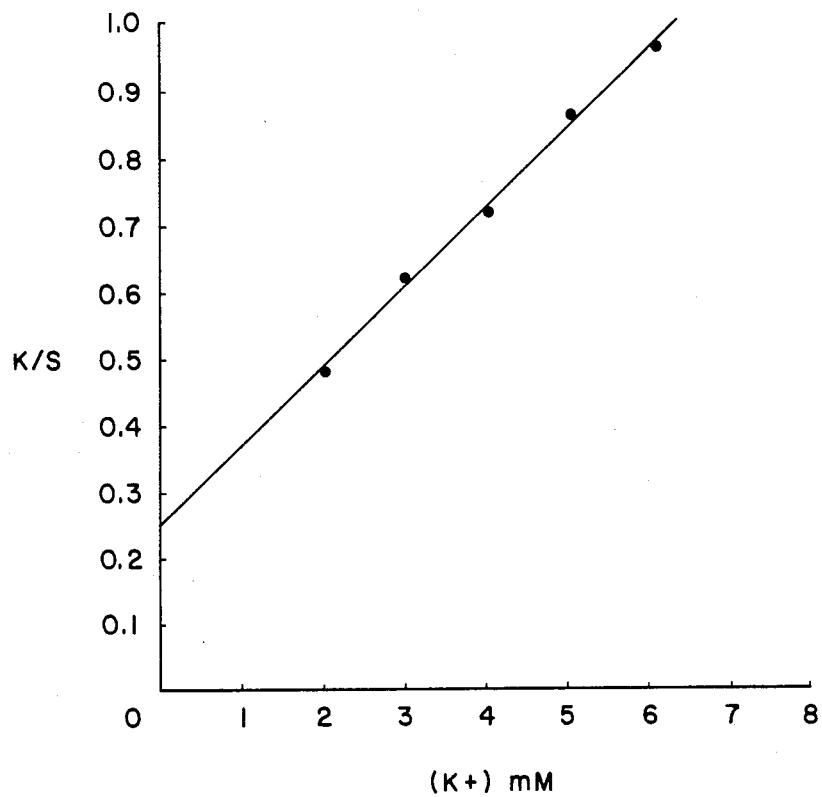

United States Patent [19]

Gantzer et al.

[11] Patent Number: 4,670,218

[45] Date of Patent: Jun. 2, 1987

[54] ION TEST MEANS HAVING A POROUS CARRIER MATRIX

[75] Inventors: Mary L. Gantzer; Paul R. Hemmes, Jr.; Daniel Wong, all of Elkhart, Ind.

[73] Assignee: Miles Laboratories, Inc., Elkhart, Ind.

[21] Appl. No.: 748,407

[22] Filed: Jun. 24, 1985

Related U.S. Application Data

[63] Continuation-in-part of Ser. No. 583,127, Feb. 24, 1984, abandoned.

[51] Int. Cl.$^4$ .................... G01N 21/78; G01N 33/52
[52] U.S. Cl. ........................................ 422/56; 427/2; 436/74; 436/79
[58] Field of Search ............. 422/56, 57, 58; 436/73, 436/79, 74, 172, 164, 169, 170; 427/2

[56] References Cited

U.S. PATENT DOCUMENTS

| | | | |
|---|---|---|---|
| 3,616,251 | 10/1971 | Lecco et al. | 422/56 X |
| 3,630,957 | 12/1971 | Rey et al. | 422/56 X |
| 3,635,679 | 1/1972 | Bloch et al. | 436/169 X |
| 3,992,158 | 11/1976 | Przybylowicz et al. | 422/58 X |
| 4,061,468 | 12/1977 | Lange et al. | 422/56 |
| 4,272,484 | 6/1981 | Lubbers | 422/68 |
| 4,272,485 | 6/1981 | Lubbers | 422/68 X |
| 4,356,149 | 10/1982 | Kitajima et al. | 422/57 X |
| 4,367,072 | 1/1983 | Vogtle et al. | 436/501 |
| 4,540,520 | 9/1985 | Charlton et al. | 260/396 N |
| 4,552,697 | 11/1985 | Yip et al. | 260/396 N |

FOREIGN PATENT DOCUMENTS

| | | |
|---|---|---|
| 0041175 | 12/1981 | European Pat. Off. . |
| 2842862 | 4/1980 | Fed. Rep. of Germany ........ 436/74 |

OTHER PUBLICATIONS

Feinstein et al, Proc. Nat. Acad. Sci., U.S.A., vol. 68, No. 9, pp. 2037–2041, Sep. 1971.
Kusnir et al., Chemical Abstracts, vol. 82, No. 51257q, 1975.
Sumiyoshi et al., Chemical Abstracts, vol. 89, 1978, No. 89:55833s.

*Primary Examiner*—Arnold Turk
*Attorney, Agent, or Firm*—Mary G. Boguslaski

[57] ABSTRACT

A test means for determining the presence of an ion in an aqueous test sample is disclosed, as well as a test device incorporating the test means, a method for preparing it and a method for using it. The test means is composed of a porous carrier matrix incorporated, substantially uniformly, with a homogeneous hydrophobic composition and with a buffering substance capable of providing a pH in the range of from about 5 to 10. The homogeneous hydrophobic composition contains an ionophore capable of forming a complex with the ion, a hydrophobic substance and a reporter substance capable of interacting with the complex of ionophore and ion to produce a detectable response. In a preferred embodiment, this invention provides a colorimetric test capable of measuring serum potassium.

23 Claims, 2 Drawing Figures

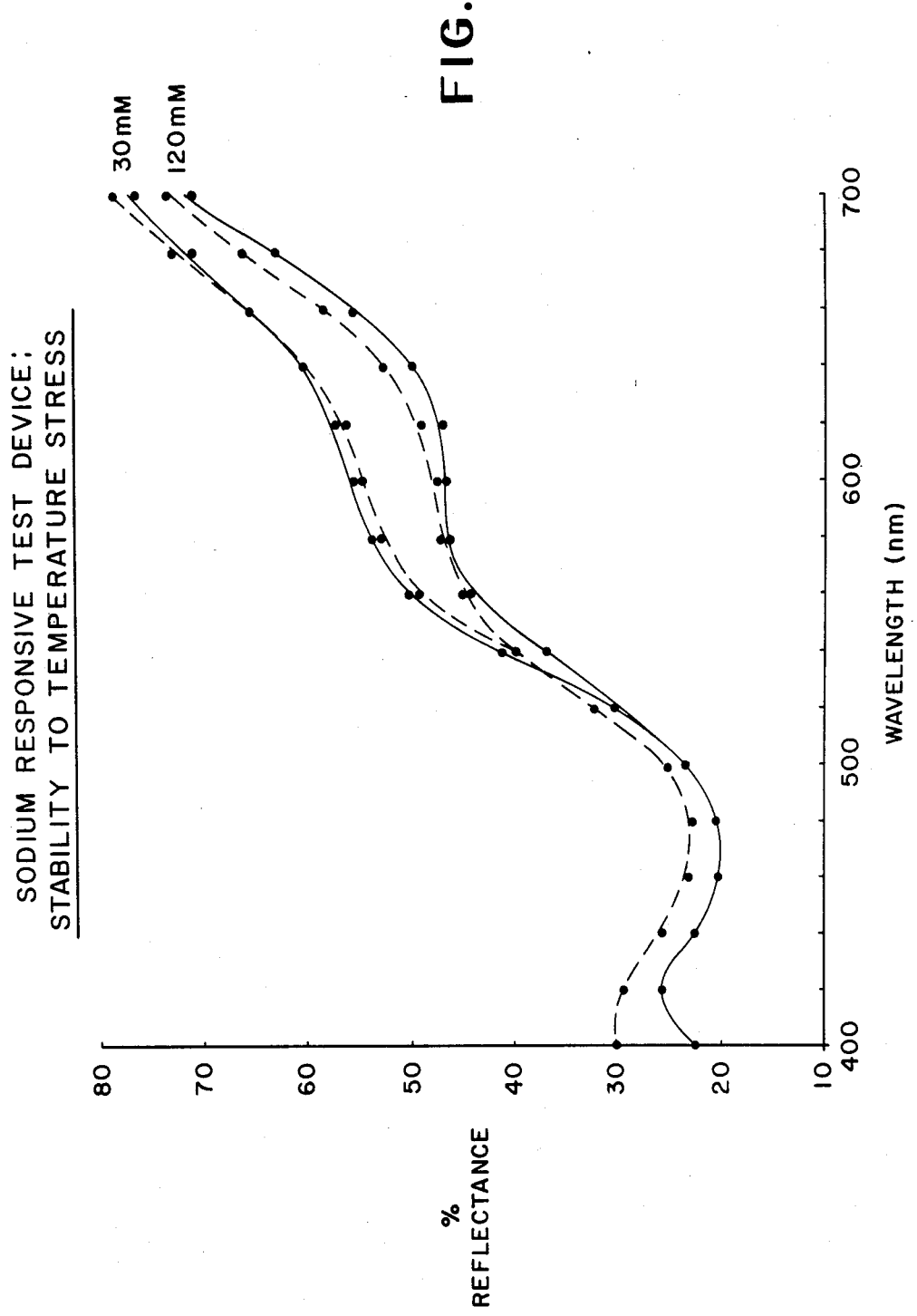

ION TEST MEANS HAVING A POROUS CARRIER MATRIX

RELATED APPLICATIONS

This application is a continuation-in-part of U.S. Ser. No. 583,127, filed Feb. 24, 1984, and now abandoned.

1. INTRODUCTION

The present invention relates to the measurement of ions, in particular ions in aqueous solution, and to a test means or device for performing such measurements. The invention provides a quick, convenient format for determining the presence and/or concentration of ions whereby results are available momentarily after contacting an aqueous test sample with the test means or device. Cumbersome, expensive electronic equipment such as ion-specific electrodes, flame photometers, atomic absorption photometers or the like, is not needed. The present invention enables the user merely to contact the test sample with a test device or similar test means configuration, and determine any detectable response.

The determination of aqueous ion concentration has application in numerous technologies. In the water purification art, calcium concentration must be carefully monitored to assess the degree of saturation of an ion exchange resin deionizer. Measurement of sodium and other ions in seawater is important in the preparation of drinking water aboard a ship at sea. Measurement of the potassium level in blood aids the physician in diagnosis of conditions leading to muscle irritability and excitatory changes in myocardial function and conditions such as oliguria, anuria, urinary obstruction and renal failure due to shock. Since the clinical range of serum potassium is only from about 2 to 10 millimolar (mM) with a normal range of from about 3.5 to 5.5 mM, these measurements require particular sensitivity and precision. Measurement of lithium levels in the blood is also important since the toxic dose levels are only slightly higher than the therapeutic levels used in psychiatric treatment.

A sensitive convenient method for determining ion concentration would greatly enhance the state of these technologies, as well as any others where such rapid, accurate determinations would be beneficial. Thus, for example, if a medical laboratory technician could accurately measure the sodium, lithium, potassium or calcium ion level of a serum or whole blood sample in a matter of seconds or minutes, such rapid results would increase laboratory efficiency and would aid the physician in diagnosis.

2. INFORMATION DISCLOSURE

Methods for determining ions in solution include flame photometry, atomic absorption photometry and ion-specific electrodes. Test strip formats have been disclosed in copending U.S. patent application Ser. Nos. 493,969, 493,983 and 493,982 assigned commonly herein. The use of certain compounds and compositions which selectively isolate ions from a sample solution has become popular in ion-specific electrodes. These substances, known as ionophores, have the capability of transporting ions into an electrode membrane causing a difference in potential which can be measured. Ion assays utilizing the ion/ionophore phenomenon include membrane electrodes, liquid/liquid partitioning, fluorescence and test strips.

2.1 Ion-Specific Electrodes

When two solutions having different concentrations of ions are separated by an electrically conductive membrane, an electrical potential (EMF) is generated. In such membrane separation cells, the membrane can be a simple fritted glass barrier, allowing a small but measurable degree of ion diffusion from one solution to the other. Alternatively, a nonporous, electrically non-conductive film, such as polyvinyl chloride, impregnated with an ionophore can be employed. In the absence of the ionophore, the film is an insulator and no EMF can be measured; when blended with an ionophore, charged ions are bound to the film and a small, measurable current can be induced to flow. Because the ionophore is selective in its affinity, and thus will bind only certain specific ions, such cells are ion selective. Any measureable EMF is due solely to the presence of the bound ions.

The current flowing across the membrane is so small that the actual quantity of ion or counterion transported is insignificant. Electrical neutrality of the membrane is maintained either by a reverse flow of hydrogen ions, or by a parallel flow of hydroxyl ions. This anion effect can reduce the specificity of the electrode towards the specific ion to be determined and is an interference to be minimized.

A major difficulty in the use of such ionselective electrodes has been a marked reduction of accuracy and speed of response over time. Further, small changes in ion concentration produce such small changes in EMF that sophisticated voltmeter equipment is required.

It has also been shown that certain antibiotics, such as valinomycin, have an effect on the electrical properties of phospholipid bilayer membranes (biological membranes), such that these antibiotics solubilize cations within the membrane in the form of mobile charged couples, thereby providing a "carrier" mechanism by which cations can cross the insulating hydrocarbon interior of the membrane. Such complexes carry charge through the membrane such that a voltage differential can be determined between solutions on either side of the membrane.

U.S. Pat. No. 3,562,129 issued to Simon, describes the use of porous membranes impregnated with macrocyclic derivatives of amino and oxy-acids in ion-selective electrodes. Materials used to form the membrane are glass frits and other porous membranes. Such electrodes are said to be effective in measuring ion activities.

U.S. Pat. No. 4,053,381, issued to Hamblen, et al., discloses similar technology, and utilizes an ion specific membrane having ion mobility across it.

U.S. Pat. No. 3,957,607, issued to Simon et al., discloses a process for the electrochemical determination of cations utilizing an electrode having a membrane containing neutral ionophores capable of forming lipid soluble complexes with the cations.

2.2 Liquid/Liquid Partitioning

Another known application of ionophores in ion determinations is through liquid/liquid partitioning. In this procedure, a hydrophobic ionophore is dissolved in an organic solvent immiscible with water. Eisenman et al., J. Membrane Biol., 1:294–345 (1969) disclose the selective extraction of cations from aqueous solutions into organic solvents by macrotetralide actin antibiotics. This technique involves shaking an organic solvent phase containing the antibiotics with aqueous solutions containing cationic salts of lipid-soluble, colored anions, such as picrates and nitrophenolates. The intensity of color of the organic phase is then measured spectrophotometrically to indicate how much salt has been extracted. Phase transfer has also been studied by Dix et al., Angew. Chem. Int. Ed. Engl., 17:857(1978) and in reviews including Burgermeister et al., Top. Curr. Chem., 69:91 (1977); Yu et al., "Membrane Active Complexones", Elsevier, Amsterdam (1974); and Duncan, "Calcium in Biological Systems", Cambridge University Press (1976).

Sumiyoshi, et al., Talanta, 24, 763–765 (1977) describes a method stated to be applicable to serum potassium determinations. In this technique serum is deproteinated by trichloroacetic acid and an indicator dye is added and shaken with a solvent such as chloroform containing valinomycin.

Partitioning of a compound is rapid and effective between liquids, as shown by Eisenman, because the mobility of the ionophore carrier and ions allows the transported species to diffuse rapidly away from the interface. Such a mechanism is normally impossible in the solid phase because of the rigidity, immobility and essentially zero diffusion of materials in a solid phase.

2.3 Fluorescent Anions

Yet another approach to the measurement of ion activity in aqueous solutions utilizes fluorescent anions. [Feinstein, et al., Proc. Nat. Acad. Sci. U.S.A., 68, 2037–2041 (1971)]. It is stated that the presence of cation/ionophore complexes in organic solvents is known, but that complex formation in purely aqueous media had not previously been detected. Feinstein, et al., demonstrated the existence of such complexes in water through the use of the fluorescent salts, 1-anilino-8-naphthalene sulfonate and 2-p-toluidinyl sulfonate. It was found that interaction of the ionophore/cation complexes with the fluorescent dyes produced enhanced fluorescence emission, increased lifetime and polarization, and significant blue-shift at the emission maxima of the fluorescence spectrum. At constant concentrations of ionophore and fluorophore, the intensity of fluorescence emission was found to be a function of cation concentration.

2.4 Chromophore-labeled Ionophore

The ion assay disclosed in U.S. Pat. No. 4,367,072 is primarily directed toward the use of a chromogenic ionophore, i.e., an ionophore covalently bound to a chromophore. A charged chromogenionophore complex, having the same charge as the ion to be determined, is also used. In use, the chromogenic ionophore or charged chromogen- ionophore complex is added to a liquid sample and the color of the solution is monitored spectrophotometrically. Mention is made of incorporating the ionophore into a carrier such as paper, synthetic resin film, silicon oxide, natural or synthetic fibers or metal.

2.5 Test Strip Format

As mentioned previously, test strip formats for ion determinations have been disclosed in copending applications commonly assigned herein. U.S. patent application Ser. No. 493,969 is directed to a nonporous nonpolar carrier matrix incorporated with an ionophore. A counterion reporter substance is added to the test sample. U.S. patent application Ser. No. 493,983 is directed to a nonporous nonpolar carrier matrix incorporated with an ionophore and a reporter substance. The present invention does not utilize a nonporous carrier matrix; to the contrary, the carrier matrix must be porous.

U.S. patent application Ser. No. 493,982 is directed to a hydrophilic carrier matrix incorporated with finely divided globules of a hydrophobic vehicle. The globules contain an ionophore and a reporter substance. They are formed by preparing an emulsion of the hydrophobic mixture and a mixture of water and a hydrophilic polymer such as gelatin. The emulsion is then coated onto a support member and the water evaporated leaving the hydrophilic polymer and the finely divided globules. The emulsion can be coated onto paper, evaporated and that carrier affixed to a support. In any case, the test means comprises finely divided globules of hydrophobic vehicle containing an ionophore and a reporter substance in a hydrophilic matrix. The present invention differs from the disclosure of the '982 application in that the ionophore and reporter substance are incorporated into a porous carrier matrix directly as a homogeneous hydrophobic composition. No emulsion is involved.

The test device format of the present invention was demonstrated at the American Association for Clinical Chemistry annual meeting on July 29 to Aug. 3, 1984.

2.6 Summary

Many methods are known for assaying ions in solution. Instrumental methods include such sophisticated techniques as ion-specific potentiometry, flame photometry and atomic absorption photometry. The use of ionophores which selectively complex with specific ions has lead to five basic approaches: ion selective electrodes, liquid/liquid partitioning, fluorescence enhancement, chromophore-labeled ionophore conjugates and test strips.

Unlike prior test formulations, this invention provides a stable unitary test means (or device) by incorporating a homogeneous hydrophobic composition with a porous carrier matrix.

3. BRIEF DESCRIPTION OF THE DRAWINGS

Performance data depicting the dose response of a test device responsive to the presence of potassium ion is portrayed graphically in FIG. 1. Data were taken using test devices formulated according to the procedure described in Example 11.5. The graph shows the calculated K/S values plotted versus concentration of potassium ion [K+], in millimoles per liter or millimolar (mM).

FIG. 2 shows reflectance spectra obtained 30 seconds after dipping test devices, prepared as described in Example 11.2, in urine containing 30 or 120 millimolar (mM) sodium ion. The small change in the spectrum for devices subjected to the stress of 1 month storage at 40° C. (dashed line) over the room temperature spectrum (solid line) indicates the stability of the sodium responsive device on a paper matrix formulated with the inclusion of buffer.

4. SUMMARY OF THE INVENTION

The present invention resides in the discovery of a new test means for detecting the presence of an ion in an aqueous test sample and determining its concentration. The test means comprises a porous carrier matrix substantially uniformly incorporated with (a) a homogeneous hydrophobic mixture containing three principal ingredients: an ionophore capable of forming a complex with a specific ion to be determined, a hydrophobic substance and a reporter substance capable of interacting with the complex of ionophore and ion to produce a detectable response; and (b) a buffering substance capable of providing a pH in the range of from about 5 to 10.

A test device comprises the test means affixed to one upper flat face of an elongated support member.

In use, the aqueous test sample is contacted with the test means or device. The presence and/or concentration of a specific ion to be determined in the test sample is then determined by observing any detectable response produced.

The test means and device of the present invention provide rapid results, sufficient detectable response forming in most instances in at least a few minutes.

5. DEFINITIONS

The following definitions are provided to clarify the scope of the present invention and to enable its formulation and use.

5.1 The term "ionophore" includes molecules capable of forming a complex with a particular ion, in some instances to the substantial exclusion of others. For example, the cyclic polyether 2,3-naphtho-1,4,7,10,13-pentaoxacyclopentadeca-2-ene (sometimes known as 2,3-naphtho-15-crown-5 and called Potassium Ionophore I herein) binds selectively to potassium ions in solution to form a cationic complex. Included in the term are coronands, cryptands and podands.

5.2 A "reporter substance" is one which is capable of interacting with an ionophore/ion complex to produce a detectable response such as a color change. A preferred reporter is a neutral compound having a dissociable proton which proton dissociates upon interaction of the reporter with an ionophore/cation complex. The reporter then becomes charged, effecting a change in electron distribution. The change in electron distribution produces a detectable response. The expression "reporter substance" includes phenolic compounds, such as p-nitrophenol, which are relatively colorless in the nonionized state, but which color upon ionization, and fluorescent compounds which produce more or less fluorescence upon a change in electron distribution. The reporter substance can also be one which can trigger a detectable response together with other components. For example, the change in electron distribution in the reporter substance caused by interaction with the complex can in turn facilitate the interaction of the reporter with another component which would then produce a detectable response.

5.3 By "interacting" is meant any coaction between a reporter substance and an ionophore/ion complex which leads to a detectable response. The interaction between an ionophore/cation complex and preferred reporters having a dissociable proton, will cause the reporter to lose a proton thus producing a detectable response.

5.4 The expression "detectable response" is meant herein as a change in or occurrence of a parameter in a test means system which is capable of being perceived, either by direct observation or instrumentally, and which is a function of the presence of a specific ion in an aqueous test sample. Some detectable responses are the change in or appearance of color, fluorescence, reflectance, pH, chemiluminescence and infrared spectra.

5.5 By the expression "intermediate alkyl" as used herein is meant an alkyl group having from about 5 to about 15 carbon atoms. It includes normal and branched isomers. It can be unsubstituted or it can be substituted, provided any such substitution not interfere with the operation of the presently claimed test means.

5.6 The expression "lower alkyl", as used in the present disclosure, is meant as an alkyl moiety containing about 1 to 4 carbon atoms. Included in the meaning of lower alkyl are methyl, ethyl, n-propyl, isopropyl, n-butyl, sec-butyl and tert-butyl. These can be unsubstituted, or they can be substituted provided any such substituents not interfere with the operation of the presently claimed test means.

5.7 By "pseudohalogen" is meant atoms or groups of atoms which, when attached to an unsaturated or aromatic ring system, affect the electrophilicity or nucleophilicity of the ring system, and/or have an ability to influence the distribution of an electrical charge through delocalization or resonance, in a fashion similar to the halogens. Thus, whereas halogen signifies Group VII atoms such as F, Cl, Br and I, pseudohalogens embrace such moieties as $-CN$, $-SCN$, $-OCN$, $-N_3$, $-COR$, $-COOR$, $-CONHR$, $-CF_3$, $-CCl_3$, $-NO_2$, $-SO_2CF_3$, $-SO_2CH_3$, $-SO_2-C_6H_5$, $-SO_2C_6H_4CH_3$, $-SOC_6H_5$ and $-SOCF_3$ in which R is alkyl or aryl.

5.8 The term "porous" as used herein refers to the availability of interstices in the carrier matrix which allow an aqueous test sample ready access to the hydrophobic composition containing the ionophore and the reporter substance. For example, paper is a porous carrier matrix which maintains an open lattice structure even after it has been incorporated with the homogeneous hydrophobic composition and additionally with the buffering substance and dried. Upon contact with the doubly incorporated and dried paper, the aqueous sample flows readily into that open network. The area of contact between the hydrophobic composition and the aqueous sample is accordingly very large.

5.9 By "homogeneous" is meant uniform dispersion of the hydrophobic components throughout the composition such that any randomly selected portion would contain about the same amount of each of the composition ingredients.

5.10 The homogeneous hydrophobic composition is incorporated with the porous carrier matrix without any intentional discontinuties. However, the porous nature of the matrix is maintained even after incorporation and drying. Therefore the expression "substantially uniformly" is used in recognition of the fact that the matrix retains openings after drying into which an aqueous test sample can flow when contacted by the test means (or device).

6. TEST MEANS

The present test means comprises three basic elements: (a) a porous carrier matrix; (b) a homogeneous hydrophobic composition containing an ionophore, a hydrophobic substance and a reporter substance; and (c) a buffering substance. When an aqueous test sample contains an ion capable of complexing with the ionophore, the ion can interact with the ionophore contained in the homogeneous hydrophobic composition producing an ionophore/ion complex which complex in turn interacts with the reporter substance to produce a detectable response. The buffering substance is directly incorporated with the porous matrix making manipulation of the test sample to adjust the pH unnecessary. The buffer dissolves in the aqueous phase created by contact with a test sample. In a preferred embodiment for the determination of a cation, the reporter is a neutral compound having a dissociable proton which proton is capable of dissociating upon interaction of the reporter with the ionophore/cation complex to produce a detectable response. It has been found that the proton is actually ejected into the aqueous phase created by the test sample. The buffer apparently functions to promote the interaction of the reporter with the complex by maintaining a proper pH in spite of the increasing proton concentration.

An interferant removal substance and a wetting substance can be added to the test means (or device). Other components including stabilizers, preservatives, thickeners [such as vinylmethyl ether/maleic anhydride copolymer (available commercially as Gantrez® M-154 from GAF Corp., New York, N.Y.), polystyrene sulfonic acid or agarose], photochemical stabilizers and so forth can be added, provided they do not interfere with the production of the detectable response. Given the present disclosure, the choice of such components is well within the skill of those knowledgeable in the art. Any component added to the hydrophobic composition should not change its essential homogeneous hydrophobic character. Additionally, the carrier matrix should retain its porous nature after incorporating all the components and drying.

The homogeneous hydrophobic composition of the present invention or the buffer substance can be incorporated with the carrier matrix in a variety of ways. The ingredients of the hydrophobic composition or of the buffer composition can be dissolved in a suitable solvent or a mixture of solvents as described herein. Such solutions can be used to impregnate the carrier matrix by immersion or as an ink wherein the reagents are printed on a suitable matrix, or the carrier matrix can be coated with the composition, such as with a doctor blade. The buffering substance is usually soluble in aqueous solutions only and must be incorporated separately from the hydrophobic composition. The preferred method is described in Section 10.1 under general procedure. With the preferred reporters having a dissociable proton, the buffer must be incorporated separately from the hydrophobic composition because the inclusion of buffer in the hydrophobic composition could cause the reporter to lose the dissociable proton and produce a detectable response without the formation of an ionophore/cation complex.

6.1 Carrier Matrix

The carrier matrix with which the homogeneous hydrophobic composition is incorporated must be able to support a hydrophobic phase in such a way that substantial openings exist after drying into which an aqueous test sample can easily move, i.e., it must be porous.

Suitable materials include paper, wood, and other cellulosic systems, sintered ceramic frits, and porous polymeric materials provided that the dimensional integrity of the matrix is maintained upon incorporation of the hydrophobic composition and subsequent contact with an aqueous sample. In addition, the matrix material cannot interact with the hydrophobic composition in a way which would interfere with the production of a detectable response.

A preferred carrier matrix is paper. For example, filter paper can be incorporated with a homogeneous hydrophobic composition and dried. The paper can also be incorporated with a buffering substance. Upon contacting the test means with an aqueous test sample, the ion can easily reach the hydrophobic phase by flowing into the open lattice of the paper. Since the buffer is incorporated directly with the test means, no sample dilution is necessary to provide the proper pH.

6.2 Hydrophobic Substance

The primary function of the hydrophobic substance is to increase the detectable response of the test means by isolating the ionophore and the reporter from the aqueous phase produced by contact with the test sample. Thus, the substance can be a liquid, a solid or combination thereof, provided that it increases the ability of the ionophore/ion complex and reporter substance to coexist in the homogeneous hydrophobic composition. It is speculated that the hydrophobic substance interacts with the ionophore/ion complex in such a way as to overcome the natural tendency of charged ions to prefer an aqueous phase and in some way stabilizes the complex when formed in the hydrophobic composition. Care must be exercised to choose a substance or combination of components to act as the hydrophobic substance which does not interfere with the interaction of the complex and the reporter. However, given the present disclosure one knowledgeable in the art will be able to choose from many compounds, or combinations thereof, which will provide a suitable hydrophobic substance.

Substances which are useful include liquids which are capable of dissolving both the ionophore and the reporter. Because a liquid could dissolve, or be leached out, into the aqueous test sample, it is preferable that the liquid be relatively insoluble in the test sample of interest.

Preferred liquids are relatively nonvolatile, i.e., have a boiling point of at least about 150° C., ideally at least about 200° C. Such liquids are normally oxygen donors, containing functional groups such as ether, ester, amide and the like or combinations thereof.

Typical liquids which fall into this category are tricresylphosphate, dioctylphthalate, tris-2-ethylhexylphosphate, di-2-ethylhexyl sebacate, n-butylacetylricinolate and nitrophenyl ethers such as 2-nitrophenyl octyl ether, 2-nitrophenyl butyl ether, dibenzyl ether and o-nitrophenyl-2-(1,3,3)-trimethyl-butyl-5,7,7-triethyl octyl ether. Mixtures of these liquids can be used.

Useful solids include cellulose/acetate, cellulose propionate, and polymers such as styrene/maleic anhydride copolymer, vinylidene chloride/acrylonitrile copolymer, styrene/allyl alcohol copolymer and poly(methyl methacrylate). Other useful polymers are poly(vinyl chloride), poly(vinylidene fluoride), polystyrene, polycarbonate, poly(4-chlorostyrene), poly(vinyl acetate), vinylidene chloride/vinyl chloride copolymer, vinyl chloride/vinyl acetate copolymer, vinyl chloride/vinyl acetate/vinyl alcohol terpolymer, polyethylene, polypropylene and polyurethane. Of course many other polymeric materials are suitable for use. The identification of such materials is well within the skill of the art, given the present disclosure.

It is possible to obtain formulations with sufficient sensitivity to produce a clinically useful ion test means using only a high boiling liquid as the hydrophobic substance, using only a solid hydrophobic substance or using a combination of such components. For example, a working formulation for lithium test means can be produced using a homogeneous hydrophobic composition containing cis-N,N,N'N'-tetraisobutyl-1,2-cyclohexane dicarboxamide (herein referred to as CDA), a reporter substance and a polymeric solid as the hydrophobic substance. In some formulations the combination of a polymer and a high boiling liquid can improve the response of the system so that a visual determination can be correlated semiquantitatively with ion concentrations. For example a presently preferred visual sodium ion test is formulated with Sodium Ionophore I, 7-decyl MEDPIN, and a combination of nitrophenyl octyl ether and poly(vinyl chloride) as the hydrophobic substance (the abbreviated terms are defined later in the specification). A preferred serum potassium test suitable for instrumental reading on a reflectance photometer such as the Ames SERALYZER ® reflectance photometer is formulated with Potassium Ionophore I, 7-decyl MEDPIN and, as hydrophobic substance, styrene/maleic anhydride copolymer.

6.3 Ionophores

The ionophore element of the present invention is a concept which is broad in scope, as characterized by the definition of the term in paragraph 5.1, supra. It includes multidentate cyclic compounds which contain donor atoms in their cyclic chains. Such multidentate cyclic compounds can be monocyclic or polycyclic. Alternatively, the ionophore can be an open chain containing donor atoms. Thus, included in the ionophore element are monocyclic ionspecific compounds known as coronands; polycyclic ion-specific compounds known as cryptands; and open chain ion-specific compounds known as podands.

6.3.1 Coronands

Coronands are monocyclic compounds containing donor atoms which are electron rich (or deficient) and which are capable of complexing with particular cations (or anions) because of their unique structures. Included in this term are crown ethers in which the monocyclic chain contains oxygen as the donor atom. Other coronands are compounds which contain an assortment of electron rich atoms such as oxygen, sulfur and nitrogen. Because of the unique sizes and geometries of particular coronands, they are adaptable to complexing with various ions. In so complexing, the electron rich atoms, such as the oxygens in a crown ether, orient towards the electron deficient cation. The carbon atom segments of the chain are simultaneously projected in a direction outwards from the ion. Thus, the resultant coronand/ion complex is charged in the center, but is hydrophobic at its perimeter. Uncharged coronands, particularly uncharged crown ethers, are preferred ionophores for the determination of potassium ion.

6.3.2 Cryptands

Cryptands are polycyclic analogues of coronands. Accordingly, they include bicyclic and tricyclic multidentate compounds. The cyclic arrangement of donor atoms is three dimensional in space, as opposed to the substantially planar configuration of coronands. A cryptand is capable of virtually enveloping the ion in three dimensional fashion and, hence, is capable of strong bonds to the ion forming the complex. As with coronands, the donor atoms can include such atoms as oxygen, nitrogen and sulfur.

6.3.3 Podands

Ions can also form complexes with noncyclic compounds. For example, a linear chain which contains a regular sequence of electron rich atoms, such as oxygen, has the capability of associating with positively charged ions to form complexes, not entirely unlike the coronands and cryptands. The main structural difference between podands and the other two ionophores is the openness of the structure. Thus, podands can be subcategorized into monopodands, dipodands, tripodands, and so on. A monopodand, therefore, is a single organic chain containing donor atoms; a dipodand is two such chains coupled by a bridge atom or group of atoms capable of variable spacial orientation; and a tripodand is three chains attached to a central atom or group of atoms. Simon et al., in U.S. Pat. No. 3,957,607, discloses dipodands particularly suited to the determination of calcium or barium ions. In the present invention, a preferred ionophore is the tripodand 1,1,1-tris[1'-(2'-oxa-4'-oxo-5'-aza-5'-methyl)dodecanyl]propane referred to herein as Sodium Ionophore I, which was found to be particularly useful in a test means for the determination of sodium ion. In fact, Sodium Ionophore I is 90 times more selective for sodium ions than the dipodand, N,N'-dibenzyl-N,N'-diphenyl-1,2-phenylenedioxydiacetamide. [Guggi, M., Oehme, M., Pretsch, E. and Simon, W., *Helv. Chim. Acta.* 59:2417(1976)]. Uncharged podands such as these are preferred ionophores for the determination of sodium and calcium ions.

6.3.4 Specific Ionophores

Some of the ionophores which have been found especially useful when used in this invention are tabulated below, along with the cations with which they are capable of selectively complexing.

Chemical names for preferred ionophores follow with their structures. Common names assigned for use herein are also noted.

| Ionophore | Cation |
|---|---|
| 1,1,1-tris[1'-(2'-oxa-4'-oxo-5'-aza-5'-methyl)dodecanyl]propane | $Na^+$ |
| [Sodium Ionophore I] | |
| N,N'—dibenzyl-N,N'—diphenyl-1,2-phenylenedioxydiacetamide | $Na^+$ |

| Ionophore | Cation |
|---|---|
| [Sodium Ionophore II] | |
| 6,7,9,10,18,19-hexahydro-17-n-butyl-dibenzo[b,k]-[1,4,7,10,13]pentaoxacyclohexadecine-18-yl-oxyacetic acid | Na$^+$ |
| [Sodium Ionophore III] | |
| 2,3-naphtho-1,4,7,10,13-pentaoxa-cyclopentadeca-2-ene | K$^+$ |
| [Potassium Ionophore I] | |
| N,N'—diheptyl-N,N',5,5-tetramethyl-3,7-dioxanonane diamide | Li$^+$ |
| [Lithium Ionophore I] | |
| N,N'—diheptyl-5,5-dimethyl-N,N'—di(3-oxapentyl)-3,7-dioxanonane diamide | Li$^+$ |
| [Lithium Ionophore II] | |
| cis-N,N.N',N'—tetraisobutyl-1,2-cyclohexane dicarboxamide (CDA) | Li$^+$ |
| diethyl-N,N'—[(4R, 5R)-4,5-dimethyl-1,8-dioxo-3,6-dioxaoctamethylene]bis(12-methylaminododecanoate) | Ca$^{++}$ |
| [Calcium Ionophore] | |

Other ionophores which are useful in the present invention include those listed below:

| Ionophore | Cation |
|---|---|
| 15-crown-5 | Na$^+$, K$^+$ |
| Valinomycin | K$^+$ |
| 4,7,13,16,21,24-hexaoxa-1,10-diaza-bicyclo[8,8,8]hexacosane (Kryptofix ® 222) | K$^+$ |
| Dibenzo-18-crown-6 | K$^+$ |
| Dicyclohexano-18-crown-6 | K$^+$ |
| 4,7,13,18-tetraoxa-1,10-diaza-bicyclo-[8,5,5]eicosane (Kryptofix ® 211) | Li$^+$ |
| 12-crown-4 | Li$^+$ |
| N,N'—diheptyl-N,N'—dimethyl-1,4- | Mg$^{++}$ |

| -continued | |
|---|---|
| Ionophore | Cation |
| butanediamide | |

Kryptofix ® is a trademark of E. Merck, Darmstadt, West Germany.

Although these specific ionophores were used advantageously in the test means of the present invention, other ionophores or mixtures thereof, can also be used. In particular, ionophores which contain ionizable groups, such as Sodium Ionophore III, can be substituted in the formulation, so long as they have sufficient analyte-ion specificity.

6.4 Reporter Substance

Given the presence of the ion of interest in the test solution, it is the reporter substance which provides the detectable response by interacting with the ionophore-/ion complex. The reporter substance can range in composition from a single compound, which can ionize in response to the formation of the ionophore/ion complex, to a mixture of reactive species which produce a detectable product when their reaction chain is triggered by the presence of the complex. Thus, it can be seen that when no analyte-ion is present, the reporter substance remains dormant and no detectable response is observed. Alternatively, when the particular ion of interest is present, a complex is formed which interacts with the reporter substance and induces it to undergo a detectable change.

In the case where the reporter is a single compound, it can include a dissociable group such that upon dissociation a colored ionic species is formed. For the determination of a cation a particularly preferred reporter is one which contains a dissociable proton such that upon interaction of the ionophore/cation complex with the reporter, the reporter loses the proton. This proton loss causes a change in, or appearance of, a detectable response in the matrix. For example, phenolic compounds such as p-nitrophenol, are relatively colorless in the nonionized state but are colored upon ionization. Tetrabromophenolphthalein alkyl esters have also been found to be useful reporters. Other compounds, such as those which produce more or less fluorescence upon a change in electron distribution, can also be used. Classes of fluorescent indicators and their derivatives which are useful in this invention include derivatives of fluorescein, especially fluorescein esters, 7-hydroxy coumarins, resorufins, pyren-3-ols and flavones.

The reporter substance can also be one which can trigger a detectable response together with other components. For example a reaction system useful as the reporter substance is one which involves the dissociation of a proton from a phenol, thus initiating a coupling reaction to form a colored product. The so-called Gibbs Reaction is typical of such a reaction sequence, in which a 2,5-cyclohexadiene-1-one-2,6-dihalo-4-haloimine (I) couples with a phenol (II) to form a colored reaction product (III).

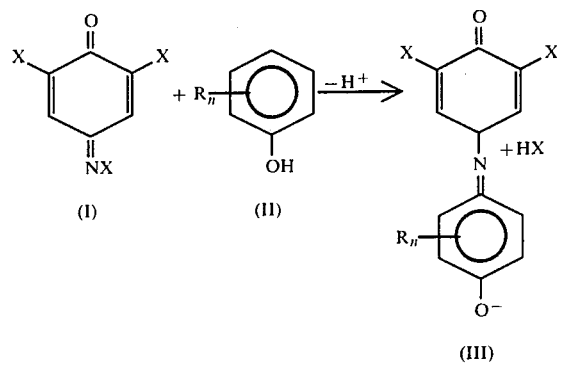

In this reaction sequence R, same or different, can be any 2,3,5 or 6-position substituent, or multiple substituents thereof, which will not hinder the overall reaction sequence. Thus each R is lower or intermediate alkyl or aryl, or one R can form a fused ring system at either the 2,3- or 5,6-positions. X is a halogen or pseudohalogen, and n is 0 to 4. X can be the same or different substituent. It is preferred, however that 2 and 6 position substituents be the same; most preferred is the trichloro substituted compound. Reporters of this type are utilized by incorporating compounds having the structures (I) and (II) with the hydrophobic composition.

Still another utilization of the Gibbs chemistry involves compounds having a structure such as (III) in its nonionized form. The formation of the ionophore/ion complex and subsequent interaction with the reporter, results in a loss of a proton such that the reporter substance (III) yields observable color in and of itself. This phenomenon can be thought of as proceeding in accordance with the following reaction sequence and resonance structures:

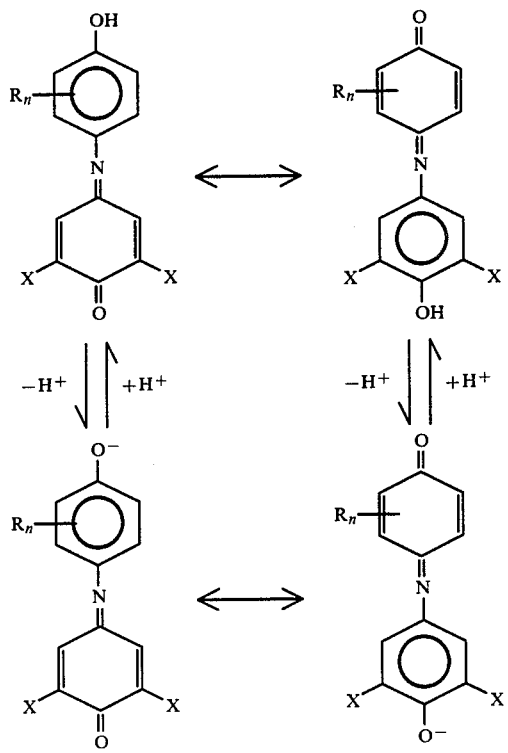

in which each R, same or different, is lower or intermediate alkyl, aryl, or multiple substituents thereof, or a fused ring system at the 2,3- or 5,6-positions, n is 0 to 4 and X is defined as above. Especially preferred is a compound having the structure

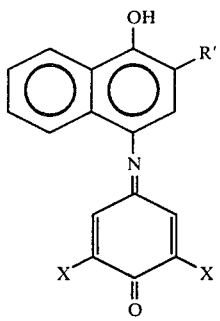

in which R' is H or lower alkyl and X is a halogen or pseudohalogen group as defined in sections 5.6 and 5.7, respectively. The case in which R' is methyl and X is a chloro group has been found especially suitable to the present invention.

Yet another preferred reporter substance is a compound having the structure

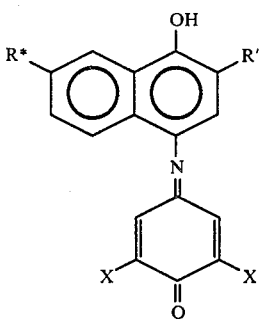

in which R* is intermediate alkyl, i.e., a group having 5 to 15 carbon atoms, and in which R' is H or lower alkyl and X is a halogen or pseudohalogen. Compounds such as these have been found to be especially resistant to possible interference due to the presence of serum albumin in the test sample. Preferred among this type of reporter substances is 7-(n-decyl)-2-methyl-4-(3',5'-dichlorophen-4'-one)indonaphthol (referred to herein as 7-decyl-MEDPIN) in which R* is n-decyl, X is a chloro group and R' is methyl. More detailed information on the use and preparation of such compounds can be found in U.S. Pat. Nos. 4,522,697 and 4,540,520, both of which are assigned to the present assignee and are incorporated herein by reference.

In general, reporters which have a dissocable proton are preferred for the determination of a cation.

6.5 Buffering Substance

The buffering substance can be any buffer, or combination of buffers, capable of providing a pH in the range of from about 5 to 10. The buffer is chosen to facilitate the coaction of the ionophore/ion complex with preferred reporters, which coaction leads to a detectable response. The buffer is intended to maintain the pH of the aqueous phase produced by contact with the test sample, within a range to facilitate the interaction of a ionophore/ion complex with preferred reporters having a dissociable proton. The interaction of the complex with the reporter causes the reporter to lose the dissociable proton. It has been found that the proton actually moves into the aqueous phase produced by the test sample. The presence of a buffer in the aqueous phase allows this mechanism to continue to provide a sensitive determination.

Suitable buffers include bis[2-hydroxyethyl]-iminotris[hydroxymethyl]methane; 1,3-bis(trishydroxymethyl)methylamino]propane; N,N-bis-(2-hydroxyethyl)glycine; tris(hydroxymethyl)aminomethane; N-[2-acetamido]-2-iminodiacetic acid; N-2-hydroxyethylpiperazine-N',3-propanesulfonic acid; 3[N-tris(hydroxymethyl)methylamino]-2-hydroxypropane-sulfonic acid; tetramethylammonium borate; and tetramethylammonium phosphate.

The preferred pH range depends on the reporter substance; therefore the choice of the buffer is determined by the reporter substance used and to some extent by the desired detectable response. For example when 7-decyl MEDPIN is used as the reporter the preferred pH range is from 6 to 8.5. However, when a reporter substance having a higher pKa for the dissociable proton is used, a higher pH range will be preferred; similarly when a reporter having a lower pKa for the dissociable proton is used, a lower pH range will be preferred. When the detectable response is a color change, the buffer can influence the degree of such detectable response, and a particular buffer can be chosen for color intensity optimization. For example, the useful color range for the reporter 7-decyl-MEDPIN occurs from about pH 6 to 8.5 where the color change is from orange to blue. A higher pH, pH 8.5–10, gives shades of dark blue which are difficult to distinguish visually, and a lower pH, pH 5–6, gives shades of pale yellow, also difficult to distinguish visually. Both pH extremes could be used with instrumental analysis, although the best instrumental precision with the Ames SERALYZER ® reflectance photometer occurs at the pH range of from about 6 to 8.5. Determination of a suitable pH is a routine laboratory experiment given the present disclosure.

6.6 Interferant Removal Substance

Body fluids normally contain many cations, such as sodium ion ($Na^+$), potassium ion ($K^+$), calcium ion ($Ca^{++}$) and magnesium ion ($Mg^{++}$). Although the ionophore will usually be chosen for its selectivity for the desired ion-analyte, in some cases the presence of other cations could interfere with the coaction of the ionophore with the desired ionanalyte. For example, Sodium Ionophore I will bind sodium ion in preference to calcium ion in a ratio of approximately 4 to 1. In samples where the ratio of sodium ion to calcium ion is less than 4 to 1, it may be necessary to prevent the interaction of calcium ion with the ionophore to ensure the proper relationship between sodium ion concentration and the detectable response. An interferant removal substance can be provided to obviate this problem.

An interferant removal substance capable of interacting with an interfering ion can be incorporated into the carrier matrix directly with the hydrophobic composition or with the buffering substance. In a preferred embodiment, the removal substance is designed to interact with an interfering cation so as to keep it in the aqueous phase or otherwise prevent cation interaction with the ionophore in the hydrophobic composition.

For example, ethylenediamine tetraacetic acid (EDTA) and ethylene glycol bis(aminoethyl)tetraacetic acid are water soluble compounds which form complexes with divalent cations, such as calcium ion. If EDTA is incorporated with a test means for the determination of sodium ion, on contact with an aqueous sample containing sodium and calcium ions, EDTA will preferentially bind $Ca^{++}$. The bound calcium ion will not substantially interfere with the formation of the ionophore/sodium ion complex. In addition, ionophores can be used to remove interfering cations if they are specific for the interfering cation and are water soluble or are modified chemically to increase their water solubility without decreasing their ability to interact with the interferant. For example, Sodium Ionophore III can be modified by the addition of solubilizing groups, such as ($-SO_3H$) groups, to the benzene rings to increase its water solubility without decreasing its ability to interact with sodium ion. Other compounds such as uramildiacetic acid and trans-1,2-diaminocyclohexane-N,N,N',N'-tetraacetic acid, can also be used advantageously.

6.7 The Wetting Substance

For some uses, the operation of the test means (or device) will be enhanced by the addition of a wetting substance. For example, when a sample is pipetted onto the test means it can form a liquid bead on the surface of the device. Any substance which will reduce the surface tension of the aqueous sample allowing the sample to flow into the interstices of the test matrix can act as a wetting substance. Of course the substance must be chosen so that it does not interfere with the formation of the ionophore/ion complex or with the coaction of the ionophore/ion complex and the reporter substance to produce a detectable response.

In some cases a wetting substance need not be added. For example, when Sodium Ionophore III is used, no additional wetting substance is necessary. When a wetting substance is to be added, the substance is preferentially incorporated either with the buffering substance or separately. Suitable wetting substances include agarose and detergents such as polyethylene-glycol-p-isooctylphenyl ether; 2-0-acetoxy-3-(perfluoroalkyl)-N-carboxymethyl-N,-N-dimethylpropylamine; polyethylene glycol-1-(2-perfluoroalkyl)ethyl ether; n-decyl-N,N-dimethyl-3-ammonio-1-propanesulfonate; N-perfluoroalkyl-N-carboxyethyl-N,N-dimethylamine and polyoxyethylene esters of fatty alcohols, in particular Brij ® 35 SP (obtained from ICI United States, Inc. Wilmington, Del.) Other detergents can be used provided they do not interfere with the production of a detectable response to the designated ion-analyte.

7. CONCENTRATION RANGES OF TEST MEANS COMPONENTS

The concentrations of the test means components are not critical to the invention provided that the concentrations of the ionophore, hydrophobic substance, reporter substance and the buffering substance are sufficient to produce the desired detectable response. For qualitative results neither the concentration of the ionophore nor the concentration of the reporter substance is tied to the concentration range of the ion-analyte to be determined.

Determination of optimum concentrations is within the ability of one skilled in the art, given the present disclosure. However, the following guidelines are provided. It is preferable that the ionophore be present in molar excess over the reporter substance (i.e., greater than 1:1 molar ratio, ionophore:reporter substance). Working concentrations of the ionophore can range from 2 gm/L to saturation. The hydrophobic substance is usually in concentrations ranging from 0.01 to 200 gm/L. The interferant removal substance and wetting substance, if added at all, are commonly only 0 to 30 gm/L. The concentration of interferant removal substance will depend on the concentration of interfering ion in the test sample of interest. For example, the concentration of calcium ion interferant with a lithium ion test is much lower than the concentration of sodium ion interferant with a lithium ion test. The concentration of removal substance will therefore vary widely. It is to be expected that approximately equimolar quantities of removal substance to interferant would be used.

The working and preferred ranges for instrumental and visual ion-responsive test devices are given below usually in gm/L and alternatively in molar quantities to obviate the differences in molecular weight of various ionophores.

| | Working | Preferred |
|---|---|---|
| Instrumental | | |
| Hydrophobic Mixture (concentration given in grams per L of organic solvent) | | |
| Ionophore | 2-200 gm/L (6-600 mM) | 5-100 gm/L (15-30 mM) |
| Reporter substance | 1-50 gm/L (2-110 mM) | 5-30 gm/L (10-70 mM) |
| Hydrophobic substance | 0.01-50 gm/L | 0.02-30 gm/L |
| Wetting substance | 0-3 gm/L | 0-2 gm/L |
| Buffer Mixture (concentrations given relate grams to concentration per L of water or water miscible solvent) | | |
| Buffer | 0.1-1 M | 0.1-0.8 M |
| Interferant removal substance | 0-30 gm/L | 10-20 gm/L |
| Wetting substance | 0-3 gm/L | 1-2 gm/L |
| Visual | | |
| Hydrophobic Mixture (concentration given in weight per final volume hydrophobic solution) | | |
| Ionophore | 2-50 gm/L (3-80 mM) | 5-15 gm/L (7-25 mM) |
| Reporter substance | .5-5 gm/L (1-11 mM) | 1.5-4 gm/L (3-9 mM) |
| Hydrophobic substance | 10-200 gm/L | 10-150 gm/L |
| Buffer Mixture (concentration in final volume buffer solution) | | |
| Buffer | 0.1-1.0 M | 0.3-0.7 M |
| Interferant removal substance | 0-30 gm/L | 0-20 gm/L |
| Wetting substance | 0-3 gm/L | 0-2 gm/L |

8. TEST DEVICE

The test means prepared as described in Section 6 can be mounted at one end of an elongated support member, the other end of the support serving as a handle, thus forming a test device. Such a test device can be held at the handle end, while the other end bearing the test means is contacted with the test sample.

Useful materials for the support member include films of a myriad of plastics or polymers. Examples include such polymeric materials as cellulose acetate, polyethylene terephthalate, polycarbonates and polystyrene. The support can be opaque or it can transmit light or other energy. When the detectable response is fluorescence or when a coating is placed over the upper surface of the test device to allow the sample to be wiped off, the test device can be read through the support material. In that case useful supports include transparent materials capable of transmitting electromagnetic radiation of a wavelength in the range of about 200 nanometers (nm) to 900 nm. The support need not, of course, transmit over the entire 200–900 nm region, although for fluorometric detection of analytical results it is desirable that the support be transparent over a band wider than, or at least equal to, the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics.

To prepare a test device of the present invention, a small rectangle of the test means, i.e., a doubly dried porous carrier matrix doubly incorporated with homogeneous hydrophobic composition containing an ionophore, a hydrophobic substance and a reporter substance, and with a buffering substance and possibly with other ingredients, is affixed to an elongated support member having an upper substantially flat face, such as an oblong piece of polystyrene film. The test means piece is affixed to the upper flat face at one end, leaving the other end of the polystyrene to serve as a convenient handle.

The test means can be affixed by any means compatible with the intended use. One method is to use a double faced adhesive tape between the test means rectangle and the support member. One such tape, known as Double Stick, is available from 3M Company, St. Paul, Minn.

9 USE OF THE INVENTION

The test means and device of the present invention can be adapted for use in carrying out a wide variety of chemical analyses, not only in the field of clinical chemistry, but in chemical research and chemical process control laboratories. They are well suited for use in clinical testing of body fluids, such as blood, blood serum, cerebrospinal fluid and urine, since in this work a large number of repetitive tests are frequently conducted, and test results are often needed a very short time after the sample is taken. A preferred use is the testing of cations such as $K^+$, $Na^+$, $Li^+$, or $Mg^{++}$. In the field of blood analysis, for example, the invention can be adapted for use in carrying out quantitative analyses for many of the blood electrolytes of clinical interest. The present invention provides a test particularly useful for the determination of serum potassium wherein a test for low concentrations of potassium requires measurements of high sensitivity and high precision.

The test means (and test device) is used by contacting it with the test sample for a sufficient period of time. In the case of urine testing merely dipping the test means (or device) into the sample is sufficient. Although it is usually unnecessary to remove excess sample, in some cases, such as whole blood samples, it is desirable to remove any excess by wiping or blotting.

If the ion under analysis is present in the test sample, the ionophore/ion complex will interact with the reporter substance, and a response will be detectable. Where the reporter is a dissociable compound producing a colored compound different from the undissociated compound, an observable color (change) will form in the test means which can be instrumentally monitored from either side of the device when a transparent support member is used. Where the reporter substance is a fluorophore such as fluorescein or its derivatives, a fluorescence spectrophotometer can be utilized to measure the detectable response formed in the test means (here, the appearance of or change in fluorescence). Other techniques useful in observing a detectable response include reflectance spectrophotometry, absorption spectrophotometry and light transmission measurements.

Various calibration techniques are applicable as a control for the analysis. For example, a sample of analyte standard solution can be applied to a separate test means as a comparison or to permit the use of differential measurements in the analysis. Test means (or devices) can be formulated which are suitable for semiquantitative visual determinations when an appropriate color chart is supplied.

10. PROCEDURE

10.1 Preparation, General

Test Means Preparation

Test means responsive to a particular ion designated as the analyte were prepared by the following method:

(a) forming a homogeneous first mixture of the hydrophobic composition containing at least an ionophore capable of forming a complex with a specific ion to be determined, a hydrophobic substance, a reporter substance capable of interacting with the complex of the ionophore and the ion to produce a detectable response and an organic solvent;

(b) forming a homogeneous second mixture of a buffering substance capable of providing a pH in the range of from about 5 to 10 and water or a watermiscible solvent or mixtures thereof;

(c) incorporating one of the first or the second mixtures with a porous carrier matrix;

(d) drying the incorporated matrix;

(e) incorporating the other of the first or second mixtures with the porous carrier matrix; and (f) drying the doubly incorporated carrier matrix.

Unless otherwise stated, the first mixture is a homogeneous hydrophobic solution prepared by dissolving the required components in an organic solvent. Suitable organic solvents include ketones and ethers, such as tetrahydrofuran, acetone and cyclohexanone, among others. Choice of a suitable solvent would be routine for one skilled in the art given the present disclosure. Although some polymers such as styrene/maleic anhydride copolymer can be used alone as the hydrophobic substance, when a high boiling liquid such as nitrophenyl octyl ether is used, the hydrophobic substance generally will include a polymer.

The second mixture is commonly an aqueous solution containing a suitable buffer, prepared by dissolving the buffer in distilled water and titrating to the desired pH. In the following examples, the buffer solution is defined in terms of its final concentration. Whatman ® type 31

ET filter paper is used as the porous carrier matrix. Each solution is incorporated into the porous carrier matrix separately. The homogeneous hydrophobic solution is preferably incorporated with the paper first by immersing the paper in the solution. The paper is then dried in an air oven. The second incorporation is accomplished by immersing the dried paper in the aqueous buffer solution; the doubly incorporated paper is again dried in an air oven. However, the order of incorporation can be changed.

Test Device Preparation

Test devices, unless otherwise stated, were prepared by affixing a piece of doubly immersed and dried paper, cut from the resulting test means, to one end of a 0.5×10 centimeter (cm) polystyrene film strip with a double-sided adhesive tape (Double Stick from 3M Co., St. Paul, Minn.) The test device thus formed is suitable for use with the Ames SERALYZER ® reflectance photometer, or for visual reading with an appropriate color chart.

10.2 Preparation, Variations

Any variation from the general procedure outlined above will be specifically noted in the examples.

In some cases the buffer solution was prepared with a water-miscible solvent, such as lower alcohols or acetone, or mixtures of water and a water-miscible solvent. For example, the buffering substance can be dissolved in distilled water, titrated to the desired pH and a mixture of water and a lower alcohol, such as methanol or ethanol, added to produce the final volume. In those cases, the buffer solution is defined in terms of its final concentration in the water/alcohol solution. When a water-miscible solvent alone is used, the buffering substance is dissolved in the solvent, titrated to a suitable pH with phosphoric acid and brought to final volume with solvent.

Normally any wetting substance and/or interferant removal substance used was included in the buffer solution and incorporated into the test means in the second impregnation.

10.3 Results

A test means (or device) was tested for its response to a designated ion-analyte by contacting the device with an aqueous sample and observing any detectable response. Contact was made either by dipping the device into a sample or by pipetting a sample onto the device. Samples were either contrived aqueous samples, urine or serum samples. When body fluid samples were used, flame photometry was employed to determine the concentration of designated ion-analyte in the sample. Reflectance measurements, taken a predetermined amount of time after contact, were related to the concentration of the ion-analyte.

When the devices were formulated for quantitative instrumental reading, reflectance was measured on an Ames reflectance photometer (Miles Laboratories, Inc. Elkhart, IN) at a wavelength between 640-700 nanometers (nm), commonly 640 nm. These reflectance measurements were evaluated with a simplified form of the well known Kubelka-Munk equation [See Gustav Körtum, "Reflectance Spectroscopy", pp. 106-111, Springer Verlag, New York (1969)]:

$$K/S = \frac{(1-R)^2}{2R}$$

in which R is the fraction of reflectance from the test device, K is a constant and S is the light scattering coefficient of the particular reflecting medium. K/S is related to the concentration of the absorbing species, usually a deprotonated reporter substance. K/S (or some power of K/S depending on the equilibrium relationship of the concentration of the absorbing species and the ion-analyte) was plotted against increasing concentration of ion-analyte [ion], in millimoles per liter (mM/L) in the test sample. Least squares linear regression analysis is used to obtain the best straight line fit to the data. Where K/S is used, the straight line is represented by the equation $$K/S = \text{Slope [ion]} + \text{intercept}$$

where [ion] is the concentration of the ion-analyte in the aqueous sample; K/S is defined as above; "slope" refers to the slope of the least squares plot; and "intercept" refers to the intercept of the least squares plot. A regression coefficient, r, is calculated and indicates the scatter of the data off the straight line. Data fitting a perfect straight line plot would have a regression coefficient of one. When some power of K/S is related to the concentration of the ion-analyte due to the equilibrium relationship of the ion with the absorbing species, that power of K/S will be used to define the equation, i.e., $(K/S)^2 = \text{slope [ion]} + \text{intercept}$. In any case the equation represents the response of the test device to increasing ion concentration and is often called the "dose response" curve.

A large slope indicates the device is highly sensitive since a small change in the concentration of the ion-analyte in the sample will produce a large change in response (i.e., color). On the other hand, the intercept (the data point where the ion-analyte concentration is zero) should be as small as possible as that point indicates the background (color) which is unrelated to the ionanalyte concentration.

Devices formulated with a high boiling liquid and a polymer as the hydrophobic substance are presently preferred for the visual semiquantitative determination of sodium ion with an appropriate color chart. These devices were evaluated using reflectance measurement taken on a Macbeth ® Colorimeter, Series 1500 (Kollmorgen Corp., Newburgh, N.Y.) at wavelengths from 400-700 nm.

These reflectance data were used to calculate the ΔE between two samples. ΔE is a measure of the total color difference between two samples in three-dimensional color space. ΔE is calculated with the following equation: [See D. B. Judd and G. Wyszecki, "Color in Business, Science and Industry", John Wiley and Sons, New York (1975)]:

$$\Delta E = [(\Delta L^*)^2 + (\Delta a^*)^2 + (\Delta b^*)^2]^{\frac{1}{2}}$$

where ΔL* is a measure of the difference in lightness between the two samples, and varies from 0 for absolute black to 100 for a perfect white; Δa* is a measure of the difference in redness-greenness between two samples; and Δb* is a measure of the difference in yellowness-blueness. The L*, a*, b* are calculated from the reflectance at wavelengths from 400-700 nm. ΔE between a negative sample (one which does not contain the ionanalyte) and a positive sample (one which does contain the ionanalyte) will increase with increasing ion concentration. For visual testing the difference between concentration levels defined on a color chart should be as great as possible to allow the human eye to distinguish between the colors produced. Two colors are usually perceived as different by the human eye if the $\Delta E$ between them is at least three color difference units (i.e., $\Delta E$ between concentration levels should be 3 or greater). The ability of the human eye to distinguish color difference will vary to some degree depending on what region of color space is involved (i.e., changes from gold to light tan and variations in grey shades may have the same $\Delta E$ and yet the former could be distinguished more easily than the latter). Of course, such a difference is not necessary if instrumental reading is to be used.

Abbreviations used in the examples are as follows:

Square brackets, [], are used to designate ion concentration in millimoles per liter (mM) in the linear regression equations. All percent concentrations are given in weight per deciliter unless otherwise indicated.

| Temperature: | °C. | degrees Centigrade |
|---|---|---|
| Length: | cm | centimeters |
| Weight: | gm | gram |
| | mg | milligram |
| Volume: | dL | deciliter |
| | mL | milliliter |
| | μL | microliter |
| | L | liter |
| Concentration: | mM | millimolar (millimoles per liter) |
| | M | molar (moles per liter) |
| | % w/v | percent weight per deciliter |
| | % v/v | percent volume per deciliter |
| Ions: | Na+ | sodium ion |
| | K+ | potassium ion |
| | Li+ | lithium ion |
| | Ca++ | calcium ion |
| | Mg++ | magnesium ion |

Abbreviations for chemical components used are given below. The ionophore designations were assigned by the present inventor for convenience only. The name is usually based on the principal ion the ionophore was used to determine. However, the ionophores commonly respond, to varying degrees, to other ions. (Structures of preferred ionophores are given in Section 6.3.4)

| Ionophores | | |
|---|---|---|
| Sodium Ionophore I | | 1,1,1-tris[1'-(2'-oxa-4'-oxo-5'-aza-5'-methyl)-dodecanyl]propane |
| Sodium Ionophore II | | N,N'—dibenzyl-N,N'—diphenyl-1,2-phenyl-enedioxydiacetamide |
| Sodium Ionophore III | | 6,7,9,10,18,19-hexahydro-17-n-butyl-dibenzo[b,k][1,4,7,10,13]pentaoxacyclohexadecine-18-yl-oxyacetic acid |
| Potassium Ionophore I | | 2,3-naphtho-1,4,7,10,13-pentaoxacyclopentadeca-2-ene |
| Lithium Ionophore I | | N,N'—diheptyl-N,N'—5,5-tetramethyl-3,7-dioxanonane diamide |
| Lithium Ionophore II | | N,N'—diheptyl-5,5-dimethyl-N,N'—di-(3-oxapentyl)-3,7-dioxanonane diamide |
| CDA | | cis-N,N,N',N'—tetra-isobutyl-1,2-cyclohexane dicarboxamide |
| Calcium Ionophore | | diethyl-N,N'—[(4R,5R)—4,5-dimethyl-1,8-dioxo-3,6-dioxaocta-methylene]bis(12-methyl-aminododecanoate) |
| Hydrophobic Substance | | |
| NPOE | | 2-nitrophenyl octyl ether |
| NPBE | | 2-nitrophenyl butyl ether |
| CDA | | cis-N,N,N',N'—tetra-isobutyl-1,2-cyclohexane dicarboxamide |
| [Those below all obtained from Aldrich Chemical Chemical Co., Milwaukee, WI. unless otherwise noted] | | |
| PVC | | polyvinyl chloride |
| low MW) | | low molecular weight |
| (very high MW) | | very high molecular weight |
| VdC/VC | | vinylidene chloride/vinyl chloride copolymer (Scientific Polymer Products, Inc., Ontario, N.Y.) |
| VdC/AN | | vinylidene chloride/acrylonitrile copolymer (Scientific Polymer Products, Inc. Ontario, N.Y.) |
| PC - I | | polycarbonate (molecular weight 20,000 to 25,000) |
| PC - II | | polycarbonate (molecular weight 33,800) |
| PC - III | | polycarbonate (molecular weight 38,100) |
| Reporter Substance | | |
| 7-decyl MEDPIN | | 7-(n-decyl)-2-methyl-4-(3',5'-dichlorophen-4'-one)-indonaphthol |
| Buffering Substance | | |
| Bis-Tris | | bis[2-hydroxyethyl]-imino-tris(hydroxymethyl)methane |
| Bis-Tris propane | | 1,3-bis[tris(hydroxymethyl)methylamino]-propane |
| Tris | | tris(hydroxymethyl)-aminomethane |
| ADA | | N—[2-acetamido]-2-iminodiacetic acid |
| HEPPS | | N—2-hydroxyethylpiperazine-N',3-propane-sulfonic acid |
| Bicine | | N,N—bis[2-hydroxyethyl] glycine |
| TMA borate | | tetramethylammonium borate |
| TMA phosphate | | tetramethylammonium phosphate |
| TAPSO | | 3[N—tris(hydroxymethyl)methylamino]-2-hydroxypropane sulfonic acid (obtained from P.L. Biochemicals, Inc., Milwaukee WI) |
| Miscellaneous | | |
| THF | | tetrahydrofuran |
| EDTA | | ethylenediamine tetraacetic acid |
| EGTA | | ethylene glycol-bis(aminoethyl)-tetraacetic acid |

| | |
|---|---|
| Triton ® X-100 | (G. Fredrick Smith Chemical Co., Columbus, Ohio) polyethylene glycol-p-isooctylphenyl ether (Sigma Chemical Co., St. Louis, MO. |
| Zonyl ® FSK | 2-0-acetoxy-3-(perfluoro-alkyl)-N—carboxymethyl-N,N—dimethylpropyl-amine (Dupont Chemical Co., Wilmington, Del. |
| Zonyl ® FSN | polyethylene glycol-1-(2-perfluoroalkyl)-ethyl ether (Dupont Chemical Co., Wilmington, Del. |
| Zonyl ® FSB | N—perfluoroalkyl-N—carboxyethyl-N,N—dimethylamine (Dupont Chemical Co., Wilmington, Del. |
| Zwittergent ® 3-10 | n-decyl-N,N—dimethyl-3-ammonio-1-propane-sulfonate, (Calbiochem-Behring, San Diego, CA. |
| Brij ® 358P | polyoxyethylene ethers of fatty alcohols (ICI United States, Inc. Wilmington, Del. |

11. EXAMPLES

The present invention will now be illustrated, but is not intended to be limited, by the following examples.

Example 11.1

Sodium Ion: Sodium Ligand I

Test means (and devices) responsive to the concentration of sodium ion in aqueous samples were prepared as described in the general procedure.

The hydrophobic solution was composed of:

| | |
|---|---|
| Sodium Ligand I | 6 mg |
| NPOE | 0.3 mL |
| PVC (low MW, 10% in cyclohexanone) | 0.6 mL |
| 7-decyl MEDPIN | 5.4 mg |
| cyclohexanone | 1.35 mL |

After the first impregnation the paper was dried at 50° C. for 40 minutes. The buffer solution contained 0.3 M Bis-Tris, pH 7.5. The second drying was done at 50° C. for 30 minutes. A 0.6×0.6 cm square of the doubly impregnated and dried paper was used to form a test device. This formulation was tested to determine if visually discernible color levels would develop when the device was dipped into an aqueous sample containing from 0 to 200 mM sodium ion. The results were positive, with the color level developed corresponding semiquantitatively to the sodium ion concentration present.

Example 11.2

Sodium Ion: A Preferred Embodiment

A preferred formulation of test means (and devices) responsive to the concentration of sodium ion in aqueous sample was prepared as described in the general procedure.

The hydrophobic solution contained:

| | |
|---|---|
| Sodium Ligand 1 | 300 mg |
| NPOE | 4.5 mL |
| PVC (high MW, 5% in THF) | 15 mL |
| 7-decyl-MEDPIN | 81 mg |
| THF | 12.75 mL |

The buffer solution contained 0.45 M Bis-Tris, pH 7.5, and 0.05% polyvinylmethyl ether (Gantrez ® M-154 from GAF Corp. New York, N.Y.). Both drying steps were done at 65° C. for 7 minutes. A 1/5×2/5 inch (0.51 by 1.02 cm) piece of the doubly dried and impregnated paper was used to form a test device.

Testing was done with urine samples containing 0, 30, 70, 120 or 200 mM sodium ion. Devices dipped in different samples could be distinguished visually. Reflectance spectra were taken 30 seconds after the devices were dipped. $\Delta E$ calculation gave the following results:

| $[Na^+]$, mM | $\Delta E$ between levels |
|---|---|
| 30 | |
| | 5.97 |
| 70 | |
| | 6.65 |
| 120 | |
| | 4.16 |
| 200 | |

Since the difference in $\Delta E$ from one concentration level to another was well over 3 units, these concentration levels could easily be visually distinguished.

Example 11.3

Sodium Ion: Alternate Ionophore

An alternate ionophore for the determination of sodium ion concentration in aqueous samples was tested using the formulation of the present invention.

Test means (and devices) were prepared as described in the general procedure, using an alternate ionophore, Sodium Ionophore II. The hydrophobic solution contained:

| | |
|---|---|
| Sodium Ionophore II | 50 mg |
| NPOE | 0.75 mL |
| PVC (low MW, 10% in cyclohexanone) | 1 mL |
| 7-decyl MEDPIN | 14 mg |
| cyclohexanone | 3.3 mL |

After the first impregnation the paper was dried at 90° C. for 20 minutes. The buffer solution was 0.3 M Bis-Tris, pH 7.5. The second drying was done at 75° C. for 20 minutes. A 1/5×2/5 inch (0.51 by 1.02 cm) piece of doubly impregnated and dried paper was used to form a test device.

When test devices were dipped in urine samples containing 14, 34, 68, 119 mM sodium ion, visually discernible color developed. Reflectance spectra were taken 2 minutes after the devices were dipped in the urine samples. $\Delta E$ calculations gave the following results:

| $[Na^+]$, mM | $\Delta E$ between levels |
|---|---|
| 14 | |
| | 8.68 |
| 34 | |

-continued

| [Na+], mM | ΔE between levels |
|---|---|
| 68 | 11.03 |
| 119 | 1.37 |

The results indicate that the human eye could distinguish between the color developed after contact with the three lower concentrations, but would not be able to distinguish the color difference between the 68 mM and 119 mM concentrations.

EXAMPLE 11.4

Sodium Ion: Order of Incorporation Changed

Test means (and devices) responsive to the concentration of sodium ion in aqueous samples were prepared. The general procedure was altered by impregnating the Whatman paper first with the buffer solution prepared in methanol and second with the hydrophobic solution. The buffer solution contained 0.3 M Bis-Tris (in methanol), pH 7.5. After impregnating with the buffer, the paper was dried at 90° C. for 20 minutes.

The hydrophobic solution contained:

| Sodium Ligand I | 40 mg |
|---|---|
| PVC (low MW, 10% in cyclohexanone) | 4.0 mL |
| NPOE | 3.08 mL |
| 7-decyl MEDPIN | 56 mg |
| cyclohexanone | 12.92 mL |

The second drying was done at 75° C. for 20 minutes. A 1/5×2/5 inch (0.51 by 1.02 cm) piece of the doubly impregnated and dried paper was used to form a test device.

When devices formulated by reversing the order of impregnation were dipped in urine samples, color was visually discernible and corresponded semiquantitatively to sodium ion concentration, [Na+], as measured by flame photometry. Reflectance spectra were taken 30 seconds after the devices were dipped in urine samples.

ΔE calaculation gave the following results:

| [Na+], mM | ΔE between levels |
|---|---|
| 21 | |
| | 2.59 |
| 51 | |
| | 12.52 |
| 101 | |

Color levels obtained for the lower concentration levels were slightly closer than 3 color units. However at low concentrations of sodium ion, this device formulation changes from gold to light tan which can be more easily distinguished visually than the same degree (ΔE between levels) of color change at higher sodium ion concentrations. For example at 100 mM sodium ion and greater this formulation exhibits varying shades of grey which are more difficult to distinguish visually.

EXAMPLE 11.5

Potassium Ion

Test means (and devices) responsive to the concentration of potassium ion in an aqueous sample were prepared according to the general procedure.

The hydrophobic solution contained:

| Potassiur Ionophore I | 50 mg |
|---|---|
| NPOB | 0.6 mL |
| VdC/AN | 300 mg |
| PC-II | 110 mg |
| 7-decyl MEDPIN | 19 mg |
| THP | 25 mL |

The buffer solution, pH 6.26, contained 500 mM ADA, 667 mM Tris and 0.3% of a surfactant, Triton ® X-100, in distilled water. Each drying step was done at 60° C. for 10 minutes. A 0.5×1.0 cm piece of the doubly impregnated and dried paper was used to prepare the test device.

Aqueous potassium chloride solutions were used as samples. For each concentration of potassium ion, device reactivities were measured in triplicate by reflectance at 640 nm and the mean K/S value calculated.

| [K+], mM | Mean K/S |
|---|---|
| 2 | 0.4750 |
| 3 | 0.6114 |
| 4 | 0.7119 |
| 5 | 0.8555 |
| 6 | 0.9592 |

Least squares analysis of the data (Mean K/S versus mM potassium ion concentration) gave the following linear relationship:

$$K/S = 0.121[K^+] + 0.238; \ r = 0.9986$$

The test device gave a positive response to the presence of potassium ion with good correlation between K/S and potassium ion concentration.

EXAMPLE 11.6

Potassium Ion: Preferred Serum Potassium Formulation

A preferred formulation for a potassium test device is as follows:

The hydrophobic solution contained:

| Tetrahydrofuran | 100 ml |
|---|---|
| Styrene/maleic anhydride copolymer (50% styrene MW = 50,000) | 1.1 grams |
| Potassium Ionophore I | 1.0 grams |
| 7-decyl MEDPIN | 350 mg |

Whatman 31 ET paper was impregnated with this solution and dried 10 minutes at 60° C. in a forced air oven.

The buffer solution contained:

| Distilled deionized water | 70 mL |
|---|---|
| Bis-Tris, free base | 11.5 grams |
| Phosphoric acid 85% | 2 mL |
| Zonyl FSK | 200 mg |
| Denatured 3A alcohol | 30 mL |

The dried paper from the 1st dip was impregnated with the buffer solution and dried at 60° C. for 10 minutes. Device reactivities were measured by reflectance at 640 nm. This material shows a dose response to potassium ion concentration in forty serum samples of:

$$K/S = 9.43 \times 10^{-2}[K^+] + 0.110$$

$$r = 0.9930$$

EXAMPLE 11.7

Potassium Ion: Ionophore Variation

A series of test means (and devices) were prepared according to the general procedure, utilizing different potassium selective ionophores.

The hydrophobic solution contained:

| Ionophore (see below) | |
|---|---|
| NPOE | 2.4 mL |
| VdC/AN | 254 mg |
| PC-II | 254 mg |
| 7-decyl MEDPIN | 76 mg |
| THF | 100 mL |

The buffer solution, pH 6.6, contained 300 mM ADA, 471 mM Tris and 0.2% of a surfactant, Triton ® X-100, in distilled water. Both drying steps were done at 60° C. for 10 minutes. A 0.5×1.0 cm piece of the doubly impregnated and dried paper was used to form test devices suitable for use with the Ames SERALYZER ® reflectance photometer.

The ionophores used in the hydrophobic solution are listed below. All were obtained from Parish Chemical Co., Orem, Utah.

| | Ionophore | |
|---|---|---|
| A | Cyclohexyl-15-crown-5 | 47.6 μL |
| B | benzo-15-crown-5 | 50.6 mg |
| C | 4-acetylbenzo-15-crown-5 | 58.6 mg |
| D | 4-(1-hydroxyethyl)benzo-15-crown-5 | 58.9 mg |
| E | 4-(1-hydroxymyristyl)benzo-15-crown-5 | 90.7 mg |
| F | 4-t-butylbenzo-15-crown-5 | 61.2 mg |
| G | Potassium Ionophore I | 60.0 mg |

Aqueous potassium chloride samples were prepared containing 0, 2, 4, 6, 8 and 10 mM potassium ion. In addition, aqueous sodium chloride samples were prepared containing 0, 40, 80, 120., 160 and 200 mM sodium ion. Each formulation was tested for response to the potassium ion samples and to the sodium ion samples. Each sample was pipetted onto a test device and reflectance measurement taken at 640 nm. Results of the least squares regression analysis of the data (calculated K/S values versus ion concentration in mM) for the response of each formulation to sodium ion and to potassium ion are tabulated below.

| Ionophore | Dose Response | Selectivity K$^+$/Na$^+$ |
|---|---|---|
| A | K/S = 0.1540 + 0.02371 [K$^+$] | 62 |
| A | K/S = 0.1440 + 0.00383 [Na$^+$] | |
| B | K/S = 0.1293 + 0.006576 [K$^+$] | 41 |
| B | K/S = 0.1255 + 0.000162 [Na$^+$] | |
| C | K/S = 0.1376 + 0.00633 [K$^+$] | 73 |
| C | K/S = 0.1437 + 0.00091 [Na$^+$] | |
| D | K/S = 0.1562 + 0.00904 [K$^+$] | 60 |
| D | K/S = 0.1477 + 0.00015 [Na$^+$] | |

| Ionophore | Dose Response | Selectivity K$^+$/Na$^+$ |
|---|---|---|
| E | K/S = 0.2901 + 0.1527 [K$^+$] | 160 |
| E | K/S = 0.1793 + 0.00096 [Na$^+$] | |
| F | K/S = 0.4253 + 0.1606 [K$^+$] | 179 |
| F | K/S = 0.1805 + 0.000896 [Na$^+$] | |
| G | K/S = 0.2734 + 0.1171 [K$^+$] | 276 |
| G | K/S = 0.1409 + 0.00042 [Na$^+$] | |

The results indicate the dose response of each formulation to sodium ion and to potassium ion. In each case the response to potassium ion was at least an order of magnitude greater than the response to sodium ion. Selectivity of each formulation for potassium ion over sodium ion was calculated as the ratio of the slope of the derived equation for potassium ion over the slope of the derived equation for sodium ion.

EXAMPLE 11.8

Potassium Ion: Serum Samples

Test means (and devices) responsive to the concentration of potassium ion were prepared by the general procedure.

The hydrophobic solution contained:

| Potassium Ionophore I | 1.875 gm |
|---|---|
| NPOE | 15 mL |
| PC-II | 3.0 gm |
| VdC/AN | 6.0 gm |
| 7-decyl MEDPIN | 0.75 gm |
| THF | 600 mL |

The buffer solution, pH 6.6., was prepared by dissolving 42.8 gm ADA, 42.8 gm of Tris, and 1.5 gm of a wetting substance Zonyl ® FSB in 750 mL of distilled water. Both drying steps were done at 60° C. for 10 minutes. A 0.5×1.0 cm piece of the doubly impregnated paper was used to prepare a test device.

Devices so prepared were tested for the response to potassium ion in serum samples. The reflectance of the test device was measured on an Ames SERALYZER ® reflectance photometer between 60 and 75 seconds after contact with the serum samples. Readings were taken at 640 nanometers.

K/S, calculated as a function of reflectance measurements, was plotted against the concentration of potassium ion (mM) in each sample (as determined by flame photometry). Least squares analysis of the data gave the relationship:

$$K/S = 0.1198 [K^+] + 0.608$$

$$r = 0.9783$$

indicating the formulation gave a good response to serum potassium concentration.

EXAMPLE 11.9

Potassium Ion: Polymer Variation

Two series of test means (and devices) were prepared by the general procedure with different polymer components of the hydrophobic substance.

The hydrophobic solution contained:

| Potassium Ionophore I | 188 mg |
|---|---|
| NPOE | 0 60 mL |

| | |
|---|---|
| polymer | 0.90 gm |
| 7-decyl MEDPIN | 75 mg |
| THF | 60 mL |

The buffer solution, pH 6.6, was prepared containing 300 mM ADA, 470 mM Tris and 0.2% of a wetting substance, Triton® X-100, in distilled water. Both drying steps were done at 60° C. for 10 minutes. A 0.5×1.0 cm piece of the doubly impregnated and dried paper was used to prepare a device.

Test means, set A, were formulated using polycarbonate (PC-II) as a polymeric component of the hydrophobic substance. A second set, B, was formulated using vinylidene chloride/acryonitrile copolymer, (VdC/AN), as a polymeric component of the hydrophobic substance. Device response to potassium ion concentration was determined by contacting a device with aqueous solutions containing 2, 3, 4, 5 or 6 mM potassium chloride and measuring its reflectance at 640 nm. Both formulations responded to the concentration of potassium ion but the reactivity, as indicated by the slope, and the background interference, as indicated by the intercept of the dose response curve, changed. Least squares linear regression analysis for each formulation gave the following dose response equations:

| | |
|---|---|
| A | $K/S = 0.2214 + 0.0510 [K^+]$; $r = 0.9642$ |
| B | $K/S = 0.4826 + 0.1662 [K^+]$; $r = 0.9886$ |

Both formulations gave a positive response to potassium ion concentration with good correlation of K/S and potassium ion concentration within the clinically significant concentration range for serum potassium. Formulation B exhibited a larger change in K/S with increasing potassium ion concentration than did formulation A.

EXAMPLE 11.10

Potassium Ion: Variation in Hydrophobic Substance

Two series of test means (and devices) were prepared by the general procedure with different hydrophobic substance formulations in which a polymer, PC-III, was used with a variety of high boiling liquid components.

The hydrophobic solution contained:

| | |
|---|---|
| Potassium Ionophore I | 150 mg |
| high boiling liquid component | 0.60 mL |
| PC-III | 126 mg |
| 7-decyl MEDPIN | 19 mg |
| THF | 25 mL |

The buffer solution contained 300 mM ADA, 470 mM Tris and 0.2% of a wetting substance, Triton® X-100, in distilled water. Test means (and devices), series A, were prepared using 2-nitrophenyl octyl ether (NPOE) as a high boiling liquid component of the hydrophobic substance. Test means (and devices), series B, were prepared using 2-nitrophenyl butyl ether (NPBE) as a high boiling liquid component.

The dose response of each series of test devices to potassium ion concentration was measured by reflectance at 640 nm using aqueous samples containing 2, 3, 4, 5 or 6 mM potassium chloride. Least squares analysis of calculated K/S values versus mM potassium concentration gave the following dose response relationships:

| | |
|---|---|
| A | $K/S = 0.2302 + 0.0747 [K^+]$; $r = 0.9995$ |
| B | $K/S = 0.3263 + 0.1150 [K^+]$; $r = 0.9962$ |

Both formulations exhibited good linear response to potassium ion concentration.

EXAMPLE 11.11

Potassium Ion: Use of High Boiling Liquid Only as Hydrophobic Substance

Test means (and devices) were prepared according to the general procedure but with only a high boiling liquid component as the hydrophobic substance.

The hydrophobic solution contained:

| | |
|---|---|
| Potassium Ionophore I | 150 mg |
| NPOE | 0.6 mL |
| 7-decyl MEDPIN | 19 mg |
| THF | 25 mL |

The aqueous buffering solution, pH 6.6, contained 0.30 M ADA and 0.47 M Tris, with 0.2% of a surfactant, Triton® X-100. The doubly impregnated and dried paper was cut and used to form test devices suitable for use with the Ames SERALYZER® reflectance photometer. The devices were prepared and the response to aqueous solutions containing 2, 3, 4, 5 and 6 mM potassium chloride was measured at 640 nanometers as described in the general procedure. Least squares analysis of K/S values (calculated from the reflectance data taken at 640 nm) versus mM potassium ion concentration gave the following dose response relationship:

$$K/S = 0.1888 + 0.0435[K^+]; r=0.998$$

The formulation showed a positive response to potassium ion concentration even without the addition of a polymer.

EXAMPLE 11.12

Lithium Ion: Lithium Ionophore II

Test means (and devices) responsive to the concentration of lithium ion were prepared as described in the general procedure.

The hydrophobic solution contained:

| | |
|---|---|
| Lithium Ionophore II | 10 mg |
| CDA | 0.75 mL |
| PVC (low MW, 10% in cyclohexanone) | 1.0 mL |
| 7-decyl MEDPIN | 14 mg |
| cyclohexanone | 3.3 mL |

The buffering solution was 0.3 M Bis-Tris, pH 7.5. Both drying steps were done at 65° for 7 minutes. A doubly impregnated and dried paper was used to form a test device.

When the devices were dipped into aqueous sample containing from 0 to 50 mM lithium ion, visually discernible color levels developed which corresponded, semiquantitatively, to the concentration of lithium ion.

The ΔEs, calculated from reflectance measurements taken 5 minutes after a device was dipped in the samples, for each lithium ion concentration tested, were:

| [Li+], mM | ΔE between levels |
| --- | --- |
| 1 | |
| | 5.91 |
| 5 | |
| | 4.61 |
| 10 | |
| | 2.31 |
| 15 | |
| | 6.24 |
| 25 | |
| | 3.82 |
| 50 | |

Concentration levels 1, 5, 15, 25 and 50 mM could readily be distinguished visually using the formulation. While 10 mM lithium ion could be distinguished from 15 mM, visual distinction of 5 mM from 10 mM would be more difficult. Of course all the concentration levels could readily be distinguished instrumentally.

EXAMPLE 11.13

Lithium Ion: A Preferred Embodiment

Test means (and devices) were prepared using Lithium Ionophore II. The hydrophobic solution was prepared by mixing 0.4 mL of a solution containing 1.008 gm CDA, 18 mg 7-decyl MEDPIN and 90 μL Lithium Ionophore II; and 14.6 mL of a solution containing 0.19 gm VdC/VC and 25 mL THF. The paper was dried for 10 minutes at 50° C. and then immersed in a buffer solution containing 0.20 M bicine, which had been adjusted to pH 8.5, and 0.5% Triton ® X-100. The doubly impregnated paper was oven dried at 60° C. for 10 minutes.

The test means were evaluated by reflectance readings for response to lithium ion concentration, with aqueous samples containing from 0 to 10 mM lithium chloride. A least squares analysis of the data [(K/S)² calculated from the reflectance measurements at 640 nm at increasing mM lithium ion concentration] gave the following relationship:

$$(K/S)^2 = 0.3146 + 0.03691 [Li^+]; r = 0.988$$

The equation derived shows that the device responds to increasing lithium ion concentration with good correlation of calculated (K/S)² and lithium ion concentration.

EXAMPLE 11.14

Lithium Ion: Alternate Buffers

Test means (and devices) were prepared as described in the general procedure. The hydrophobic solution was prepared as described in Example 11.12. The buffer solution contained 0.3 M HEPPS, pH 7.5.

Evaluation on a Macbeth ® colorimeter 5 minutes after devices were dipped into aqueous samples containing lithium ion gave the following results:

| [Li+], mM | ΔE between levels |
| --- | --- |
| 10 | |
| | 5.07 |
| 25 | |
| | 6.33 |
| 50 | |

A second set of test devices was prepared using a buffer solution containing 0.2M Tris, pH 7.5. Similar evaluation procedures on aqueous samples containing lithium ion gave the following results:

| [Li+], mM | ΔE between levels |
| --- | --- |
| 10 | |
| | 6 |
| 25 | |
| | 5.61 |
| 50 | |

Both formulations exhibited approximately the same color change from one sample concentration to the next, but as indicated in Section 6.5 the choice of buffer affected the color development.

EXAMPLE 11.15

Lithium Ion: Removal of Calcium Ion Interference

Test means (and devices) responsive to the presence of lithium ion were prepared with the addition of ingredients intended to eliminate calcium ion interference. Serial impregnation and drying of Whatman filter paper was used to prepare the test means.

The hydrophobic solution was prepared by mixing 0.4 mL of a solution containing 90 μL Lithium Ionophore I, 1.004 gm CDA and 9 mg 7-decyl MEDPIN with 14.6 mL of a solution containing 19 mg VdC/AN and 25 mL THF. The paper was immersed in the hydrophobic solution and dried. The dried paper was then immersed in a solution containing 1% agarose and 0.2% Triton ® X-100 and dried. The doubly dried paper was immersed in a third solution, pH 8.50, containing the buffering substance and interferant removal substance, composed of 0.46 M Tris, 0.05 M MgSO₄.7H₂O (magnesium sulfate heptahydrate), 0.1% Triton ® X-100 and 0.05 M EGTA. After the third impregnation the paper was dried again. A piece of the triply impregnated and dried paper was used to form test devices suitable for use with an Ames SERALYZER ® reflectance photometer. Samples containing 0, 2, 4, 6, 8 or 10 mM calcium chloride were pipetted onto the devices. Reflectance measurements at 640 nm on reacted devices were used to calculate (K/S)². The calculated values were then used in a least squares linear regression analysis to determine if the devices containing the calcium interferant removal substance responded to the presence of calcium ion. The dose response equation obtained was:

$$(K/S)^2 = 0.1488 - 9.77 \times 10^{-5} [Ca^{++}]; r = -0.068$$

indicating that the presence of calcium ion has no effect on devices formulated with the calcium ion interferant removal substance.

EXAMPLE 11.16

Lithium Ion: Ionophore as the Interference Removal Substance

Test means (and devices) responsive to the presence of lithium ion are prepared as described in Example 11.13. To reduce the interference of sodium ion in the coaction of a lithium ionophore with lithium ion, a water soluble sodium specific ionophore such as

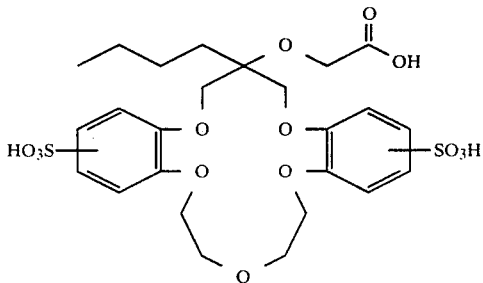

is incorporated into the paper with the buffering solution. The water soluble ionophore is produced by the chemical addition of solubilizing groups, such as —SO₃H, to an ion-specific ionophore in such a way that the chemical modification does not interfere with the formation of the desired ionophore/ion complex. The coaction of sodium ion with the interferant removal ionophore in the aqueous phase will retain the sodium ion in the aqueous phase and prevent the interfering ion from entering the hydrophobic phase, where it could interact with the lithium ionophore.

Other cation interferences are removed by utilizing suitably selective ionophores which can be made water soluble by chemical modification.

EXAMPLE 11.17

Calcium Ion

An early formulation of test means (and devices) was prepared as described in Example 11.3.

The hydrophobic solution contained:

| Calcium Ionophore | 20 mg |
| --- | --- |
| NPOE | 0.75 mL |
| PVC (low MW, 10% in cyclohexanone) | 1.0 mL |
| 7-decyl MEDPIN | 14 mg |
| cyclohexanone | 3.3 mL |

The buffering solution contained 0.3 M Bis-Tris propane, pH 7.5, in distilled water. A piece of doubly impregnated and dried paper was used to form a device as described in the general procedure.

The results of instrumental evaluation on the Macbeth ® colorimeter, 30 seconds after dipping the devices in prepared aqueous solutions containing calcium ion, were:

| [Ca$^{++}$], mM | ΔE between levels |
| --- | --- |
| 5 | |
| | 5.23 |
| 15 | |
| | 3.50 |
| 20 | |

The results indicate that the formulation can be used to prepare devices for visual correlation with the semi-quantitative concentration of calcium ion in aqueous solution ranges.

EXAMPLE 11.18

Calcium Ion: A Preferred Embodiment

Test means (and devices) were prepared by serial impregnation and drying as described in the general procedure, except that EGTA, a strong water-soluble calcium binder, was added to the buffering solution (second impregnated solution). The concentration of EGTA was adjusted so that the test device would not respond to the presence of calcium ion until the ion concentration reached 1 mM. This was expected to allow the test device to operate with higher precision over the desired concentration range.

The hydrophobic solution contained:

| Calcium Ionophore | 225 mg |
| --- | --- |
| Styrene/Maleic Anhydride copolymer 50:50) | 200 mg |
| Tricresyl phosphate | 0.75 |
| 7-decyl MEDPIN | 200 mg |
| THF | 17 mL |

The buffering solution was prepared by dissolving 129.65 g of TAPSO and 95 mg of EGTA in about 750 mL of distilled water. The pH of the mixture was titrated to 7.4 with lithium hydroxide. The final volume of the mixture was adjusted to 1 liter. The final buffering solution thus contained 500 mM TAPSO and 0.5mM EGTA, with a pH of 7.4.

A piece of the doubly impregnated dried paper was used to form a test device. The devices were tested on aqueous calcium chloride solutions containing from 0 to 5 mM calcium ion. Reflectance measurements were taken at 640 nm on an Ames SERALYZER ® reflectance photometer. A least squares linear regression analysis was preformed on the data. The dose response thus determined was:

$$(K/S) = -0.1102 + 0.2394[Ca^{++}]; \ r = 0.999$$

The negative intercept is due to the computed extrapolation of the dose-response curve that showed no response until the concentration of calcium ion reached about 1 mM. The results indicated that the test device showed good linear response to calcium ion from 1 mM to at least 5 mM, providing the high precision required for serum calcium determinations.

EXAMPLE 11.19

Magnesium Ion

Test means (and devices) were prepared by serial impregnation and drying as described in the general procedure, using the magnesium ionophore N,N'-diheptyl-N,N'-dimethyl-1,4-butanediamide available from Fluka Chemical Co.

The hydrophobic solution contained:

| 7-decyl MEDPIN | 72 mg |
| --- | --- |
| magnesium ionophore | 250 mg |
| cellulose acetate | 150 mg |
| THF | 15 mL |

The buffering solution contains 200 mM Tris buffer (pH 8.5) and 0.07% weight/volume Zonyl FSK. Whatman 31 ET paper is first impregnated with the hydrophobic solution and dried at 50° C. for 5 minutes. After a second impregnation with the buffering solution, the doubly incorporated paper is dried again at 50° C. for 10 minutes.

Test devices so formulated will show a positive, linear response to magnesium ion. Possible interference with a magnesium determination by calcium ion can be overcome by including an appropriate level of EGTA in the test sample for clinical serum samples, 2 to 3 mM EGTA would be appropriate.

Obviously many other modifications and variations can be made without departing from the spirit and scope thereof of the invention.

What is claimed is:

1. A test means for determining the presence of an ion in an aqueous test sample, the test means comprising a carrier matrix having a porous structure substantially uniformly incorporated with
   (a) a homogeneous hydrophobic composition containing an ionophore capable of forming a complex with a specific ion to be determined, a reporter substance capable of interacting with the complex of the ionophore and the ion to produce a detectable response and a hydrophobic substance; and
   (b) a buffering substance capable of providing a pH in the range of from about 5 to 10; the porous structure of the matrix being maintained after the incorporation and drying wherein an aqueous sample flows readily into the carrier matrix upon contact.

2. The test means of claim 1 in which the porous carrier matrix is additionally incorporated with an interferant removal substance capable of interacting with an interfering ion.

3. The test means of claim 1 in which the porous carrier matrix is additionally incorporated with a wetting substance.

4. The test means of claim 1 in which the porous carrier matrix is paper.

5. A test means for determining the presence of a cation in an aqueous test sample, the test means comprising a carrier matrix having a porous structure substantially uniformly incorporated with
   (a) a homogeneous hydrophobic composition containing an ionophore capable of forming a complex with a cation to be determined, a neutral reporter substance having a dissociable proton which proton is capable of dissociating upon interaction of the reporter with the complex of the ionophore and the cation to produce a detectable response and a hydrophobic substance; and
   (b) a buffering substance capable of providing a pH in the range of from about 5 to 10;
   the porous structure of the matrix being maintained after the incorporation and drying wherein an aqueous test sample flows readily into the carrier matrix upon contact.

6. The test means of claim 5 in which the reporter substance is one capable of producing the appearance of, or change in, fluorescence in the presence of the complex of the ionophore and the ion.

7. The test means of claim 6 in which the reporter substance is fluorescein or a derivative thereof.

8. The test means of claim 1 in which the specified cation to be determined is sodium ion or calcium ion and the porous carrier matrix is paper.

9. The test means of claim 8 in which the ionophore is an uncharged podand.

10. The test means of claim 5 in which the reporter substance is one capable of producing the appearance of, or change in, color in the presence of the complex of the ionophore and the cation.

11. The test means of claim 10 in which the reporter substance is a compound having the structure

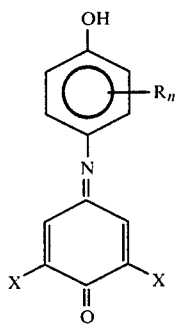

in which X, same or different, is a halogen or pseudohalogen; in which each R, same or different, is a 2-, 3-, 5-, or 6-position substituent, or multiple substituents thereof, selected from lower alkyl, intermediate alkyl, aryl or a fused ring at the 2,3- or 5,6-positions; and n is 0 to 4.

12. The test means of claim 10 in which the reporter substance is a compound having the structure

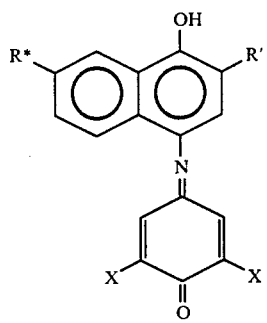

in which R' is H or lower alkyl, R* is H or intermediate alkyl and X, same or different, is halogen or pseudohalogen.

13. The test means of claim 12 in which R' is methyl and R* is n-decyl.

14. The test means of claim 13 in which the specific cation to be determined is potassium ion, the porous carrier matrix is paper and the ionophore is an uncharged crown ether.

15. The test means of claim 14 in which the uncharged crown ether is 2,3-naphtho-1,4,7,10,13-pentaoxacyclopentadeca-2-ene.

16. The test means of claim 15 in which the hydrophobic substance is styrene/maleic anhydride copolymer.

17. A test means for determining the presence of an ion in an aqueous test sample, the test means comprising a porous, fibrous carrier matrix having an open lattice structure substantially uniformly incorporated with
   (a) a homogeneous hydrophobic composition containing:
      (i) an ionophore capable of forming a complex with a specific ion to be determined;
      (ii) a reporter substance capable of interacting with the complex of the ionophore and the ion to produce a detectable response; and
      (iii) a hydrophobic substance; and
   (b) a buffering substance capable of providing a pH in the range of from 5 to 10;
   wherein the open lattice structure of the fibrous matrix is maintained after incorporation with the hydrophobic composition and buffering substance, allowing a sample to flow readily into the matrix upon contact.

18. The test means of claim 17 in which the reporter is a neutral compound having a dissociable proton which proton is capable of dissociating upon interaction of the reporter with the complex of the ionophore and the ion to produce the detectable response.

19. A method for preparing a test means for determining the presence of an ion in an aqueous test sample, the method comprising the steps of
   (a) forming a homogeneous first mixture of the hydrophobic composition comprising an ionophore capable of forming a complex with a specific ion to be determined, a reporter substance capable of interacting with the complex of the ionophore and the ion to produce a detectable response, a hydrophobic substance and an organic solvent; and
   (b) forming a homogeneous second mixture of a buffering substance capable of providing a pH in the range of from about 5 to 10 and water or a water-miscible solvent or mixtures thereof;
   (c) substantially uniformily incorporating a carrier matrix having a porous structure with one of the first or the second mixtures;
   (d) drying the incorporated matrix;
   (e) substantially uniformily incorporating the porous carrier matrix with the other of the first or second mixtures to form a doubly incorporated matrix; and
   (f) drying the doubly incorporated carrier matrix; wherein the porous structure of the matrix is maintained after incorporation of the hydrophobic composition and buffering substacne and drying so that an aqueous test sample flows readily into the matrix upon contact.

20. The method of claim 19 in which the second mixture additionally contains an interferant removal substance capable of interacting with an interfering ion.

21. The method of claim 19 in which the second mixture additionally contains a wetting substance.

22. The method of claim 19 in which the porous carrier matrix is paper.

23. The method of claim 19 in which the specific ion to be determined is a cation and the reporter is a neutral compound having a dissociable proton which proton is capable of dissociating upon interaction of the reporter with the complex of the ionophore and the cation to produce detectable response.

* * * * *